United States Patent [19]

Tour et al.

[11] Patent Number: 5,026,894

[45] Date of Patent: Jun. 25, 1991

[54] COMPOUND FOR USE IN THE SYNTHESIS OF SEMICONDUCTING POLYMERS WITH PERPENDICULARLY ARRANGED CORES AND METHOD OF SYNTHESIZING SAID COMPOUND

[75] Inventors: James M. Tour; Ruilian Wu; Jeffry S. Schumm, all of Columbia, S.C.

[73] Assignee: University of South Carolina, Columbia, S.C.

[21] Appl. No.: 492,549

[22] Filed: Mar. 12, 1990

[51] Int. Cl.⁵ .................... C07C 303/00; C07C 22/00; C08G 76/06
[52] U.S. Cl. ........................................ 558/46; 528/10; 528/12; 528/14; 528/23; 570/183
[58] Field of Search ..................... 570/184, 10, 12, 14, 570/23

[56] References Cited

PUBLICATIONS

Chem. Letters, "Synthesis of a Conformationally Restricted Porphyrin . . . Spacer", Osuka, pp. 741–744, 1989.
Helv. Chim. Acta., "Intramol. Transfer of Electronic Excitation Energies in Spiro Compounds", 55(2), pp. 658–669.
Aviram, J. Am. Chem. Soc., 110, (1988), pp. 5687–5692.
Clarkson, J. Am. Chem. Soc., (1930), pp. 2881–2891.
Weisburger, J. Am. Chem. Soc., (1950), pp. 4253–4255.

*Primary Examiner*—Harold D. Anderson
*Assistant Examiner*—T. Mosley

[57] ABSTRACT

The stereochemical structure necessary for preparation of perpendicularly arranged cores is provided by a compound of the formula

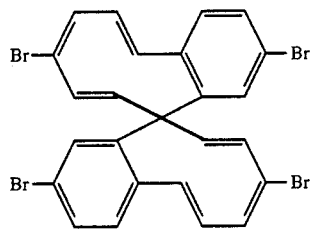

This compound can be synthesized by the reaction of

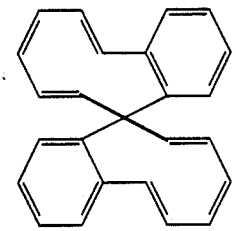

with bromine in the presence of $FeCl_3$.

4 Claims, No Drawings

COMPOUND FOR USE IN THE SYNTHESIS OF SEMICONDUCTING POLYMERS WITH PERPENDICULARLY ARRANGED CORES AND METHOD OF SYNTHESIZING SAID COMPOUND

The U.S. Government has a paid-up license in this invention and the right in limited circumstances to require the patent owner to license others on reasonable terms as provided for by the terms of Grant No. N00014-89-J-3062 awarded by the Office of Naval Research.

BACKGROUND OF THE INVENTION

This invention relates to a spiran compound with a defined physical structure for use in forming semiconducting polymers with perpendicularly arranged cores, and to a method of synthesizing this compound.

Conducting organic and organometallic polymers have attracted much recent scientific interest, since they may play a key role in the construction of modern electronic systems. In simple devices, polymers constructed from simple monomer subunits may be sufficient. As electronic component design becomes more complex and more precise, however, more complex monomer units become required to meet the needs of such systems.

As an example, it has been suggested based on calculations that a polymeric compound of the formula

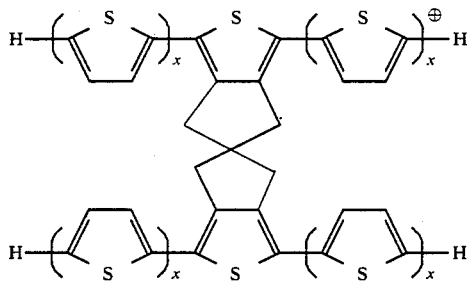

may be suitable for incorporation into future electronic devices. Aviram, A., J. Am. Chem. Soc. 110, 5687 (1988). In this compound, a pro-conducting (non-doped or non-oxidized and hence insulating) polymer is fixed at a 90° angle via a non-conjugated sigma bond network to a conducting (doped or oxidized) polymer. Such a polymeric compound would be useful in memory, logic and amplification computing systems. This compound has not actually been synthesized, however, and thus perpendicularly arranged cores of this type are not actually available.

It is an object of the present invention to provide a molecule which forms the central building block for synthesis of perpendicularly arranged cores.

SUMMARY OF THE INVENTION

In accordance with the invention, the stereochemical structure necessary for preparation of perpendicularly arranged cores is provided by a compound of the formula

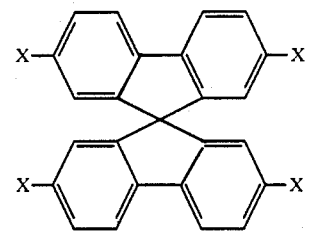

wherein X is a reactive group through which polymeric subunits can be bonded to the compound. For example, X may be Br, I, or $-O-SO_2-CF_3$ (OTf or O-triflate).

The bromo compound can be synthesized by the method of the invention in which the unsubstituted spiran of the formula

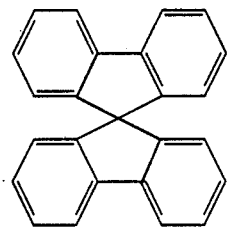

is reacted with bromine in the presence of $FeCl_3$ catalyst to yield the tetrabromo compound in 100% yield.

DETAILED DESCRIPTION OF THE INVENTION

The compound of the invention can be synthesized from

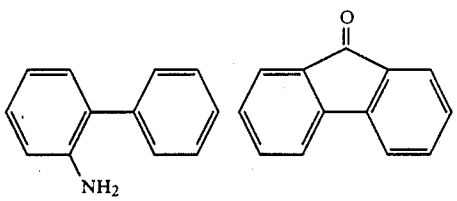

in accordance with the following series of reactions:

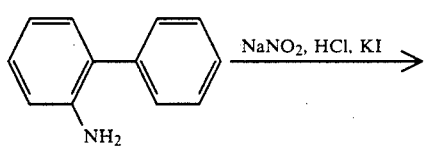

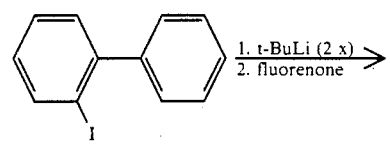

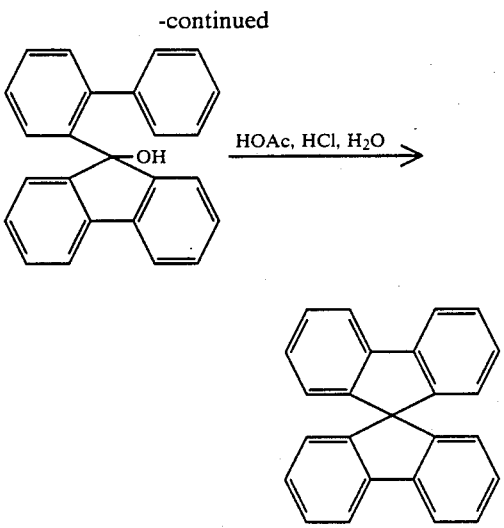

Thus, amino biphenyl is converted to the iodide by reaction with NaNO₂, HCl and KI (Sandmeyer process). Lithium halogen exchange and treatment with fluorenone yields the alcohol, which is converted to the spiro compound upon treatment with acid. The tetrabromo-compound is formed, at a surprising yield of 100%, by reaction of this spiro compound with bromine in the presence of FeCl₃. The compound in which X is I can be formed by reacting the unsubstituted compound with iodine and AlCl₃. The compound in which X is OTf can be formed by starting with a phenolic moiety, rather than the benzene moiety and reacting the phenol OH group with PhN(SO₂CF₃)₂ (phenylbistriflylamine).

The compound of the invention is intended for use as a core structure to define the stereochemistry of perpendicularly arranged polymers. The preparation of such polymers will involve the addition of polymer subunits (monomers or possibly prepolymers) to the core compound of the invention. This can be accomplished, for example, by the following reaction:

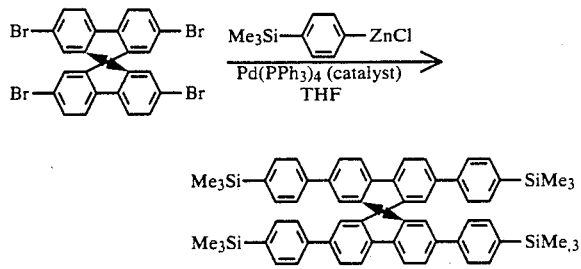

in which additional phenyl moieties are added to each of the bromine groups on the core compound. The reaction conditions, in which 1-bromo-4-(trimethylsilyl)benzene is added using palladium tetrakis(triphenylphosphine) as a catalyst in a zinc promoted reaction, are similar to those described by Negishi et al., Heterocycles 18, 117 (1982). The product can be further extended by converting the SiMe₃ groups to bromo groups by reaction with bromine and again reacting the bromo compound with 1-bromo-4-(trimethylsilyl)benzene.

Experimental Procedures

2-Iodo-1-phenylbenzene was prepared in accordance with the procedure of Heaney and Millar, Org. Syn 40:105 (1960), was used as follows. To a solution of 2-aminobiphenyl (2.53 g, 15.0 mmol) in concentrated hydrochloric acid (3 mL) and water (15 mL) at 0° C. was added sodium nitrite (1.17 g, 17.0 mmol) in water (5 mL). The temperature was held at 0° C. throughout the addition. The resulting brown solution was stirred for 45 min at 0° C., and then poured into potassium iodide (4.9 g, 30.0 mmol) in water (50 mL). The solution was stirred overnight and then extracted with ether (4×). The combined organic layers were washed with 3N hydrochloric acid (3×10 mL) and dried over magnesium sulfate to afford 3.57 g (85%) of the desired compound as a dark purple liquid. IR (neat) 3055.7, 1578.4, 1460.0, 1426.6, 1016.7, 1004.1, 746.9 cm⁻¹. ¹H NMR (300 MHz, CDCl₃)δ 7.95 (dd, J=8.1, 1.2 Hz, 1H), 7.34 (m, 7H), 7.03 (tt, J=7.3, 1.9 Hz, 1H). ¹³C NMR (20 MHz, CDCl₃)δ 146.3, 143.9, 139.3, 129.9, 129.1, 128.6, 128.0, 127.8, 127.5, 98.6. Calc'd for C₁₂H₉I:279.9749. Found: 279.9739.

9-(2'-Biphenyl)-9'-fluorenol was prepared using a modification of the procedure of Clarkson and Gomberg, J. Am. Chem. Soc. 52: 2881 (1930) as follows. To a solution of 2-iodobiphenyl (4.93 g, 17.6 mmol) in ether (20 mL) was added at −78° C., t-butyllithium (22.8 mL, 38.7 mmol, 1.7M in pentane) over 30 min. The resulting slurry was stirred at −78° C. for 1 h, and 9-fluorenone (3.17 g, 17.6 mmol) was added in ether (15 mL) over 10 min. The solution was warmed to room temperature for 30 min and poured into water. The aqueous layer was extracted with ether (3×15 mL), and the combined organic layers were washed with brine and dried over magnesium sulfate. The crude product was recrystallized from ethanol to afford 5.06 g (86%) of the desired product as a white solid. IR (KBr) 3590, 3063, 3023, 1450, 1344, 1160 cm⁻¹. ¹H NMR (300 MHz, CDCl₃)δ 8.45 (d, J=8.0 Hz, 1H), 7.51(t, J=7.4, 1.5 Hz, 1H), 7.2–7.1 (m, 1H), 6.88 (dd, J=7.5, 1.4 Hz, 1H), 6.80 (td, J=7.5, 1.3 Hz 1H), 6.58 (br t, J=7.9 Hz, 2H), 5.98 (dd J=8.1, 1.1 Hz, 2H), 2.2 (s, 1H).

9,9'-Spirobifluorene was prepared using the procedure of Clarkson and Gomberg as follows. To a solution of 9-(2-biphenyl)-9-fluorenol (11.8 g, 35.3 mmol) in refluxing acetic acid was added concentrated hydrochloric acid (0.1 mL) and the solution heated to reflux for 20 min. The solution was cooled to room temperature, and water (50 mL) was added. The resulting white solid was filtered and washed with water and dried in vacuo. No further purification was required to afford 10.9 g. (98%) of the desired compound as a white solid. IR (KBr) 3038.2, 3011.0, 1654.2, 1560.1, 1447.6, 749.3 cm⁻¹. ¹H NMR (500 MHz, CDCl₃)δ 7.82 (d, J=7.7 Hz, 4H), 7.34 (t, J=7.5 Hz, 4H), 7.08 (t, J=7.5 Hz, 4H), 6.71 (d, J=7.6 Hz, 4H).

2,2',7,7'-Tetrabromo-9,9'-spirobifluorene was prepared as follows. To a solution of 9,9'-spirobifluorene (0.316 g 1.0 mmol) in chloroform (1.5 mL) at 0° C. was added ferric chloride (8 mg, 0.05 mol) and bromine (0.4 mL, 4.1 mmol). The solution was warmed to room temperature and stirred for 3 h. The resulting slurry that formed was poured into water and washed with saturated sodium thiosulfate until the red color disappeared. The aqueous layer was extracted with methylene chloride (2×) and the combined organic layers were dried over magnesium sulfate to afford 0.63 g (100%) of the title product as a white solid. IR 3051.6, 1594.7, 1570.8, 1450.1, 1396.2, 1249.3, 1059.7, 950.6 cm$^{-1}$. $^1$H NMR (300 MHz, CDCl$_3$)δ 7.67 (d, J=8.4 Hz, 4H), 7.5 (dd, J=8.2, 1.8 Hz, 4H), 6.8 (d, J=1.5 Hz, 4H). $^{13}$C NMR (75 MHz, CD$_2$Cl$_2$)δ 149.3, 140.2. 132.1, 127.7, 122.4, 122.3, 65.7. Calc'd for C$_{25}$H$_{12}$Br$_4$: 631.7632. Found: 631.7630. Calc'd for C$_{25}$H$_{12}$Br$_4$: C, 47.51; H, 1.91. Found: C, 47.01; H, 1.97.

2,2',7,7'-Tetrakis(p-trimethylsilylphenyl)-9,9'-spirobifluorene (unoptimized). To a solution of 4-(trimethylsilyl)bromobenzene (1.88 g, 8.2 mmol) in ether (15 mL) was added at −78° C. t-butyllithium (10.1 mL, 17.2 mmol, 1.7M in pentane). The solution was stirred at −78° C. for 1 h and transferred via cannula into anhydrous zinc chloride (1.56 g, 11.5 mmol) in THF (10 mL) at room temperature. The resulting slurry was stirred for 1 h at room temperature and then transferred via cannula into tetrakis(triphenylphosphine)palladium(0) [made from tris(dibenzylideneacetone)bispalladium(0) chloroform complex (15 mg, 0.014 mmol), and triphenylphosphine (26 mg, 0.1 mmol) in THF (2 mL)] and 2,2',7,7'-tetrabromo-9,9'-spirobifluorene (0.312 g. 0.5 mmol) in THF (5 mL). The solution was heated to 55° C. for 16 h and cooled to room temperature. The solution was poured into water and the aqueous layer was extracted with chloroform (3×5 mL). The combined organic layers were rinsed with 3N hydrochloric acid, and then water, before drying over magnesium sulfate. The solvent was removed in vacuo and the resulting solid was purified by flash chromatography on silica gel with hexane (4 column volumes) followed by 30:1 hexane:ether to aford 0.18 g (40%) of the title compound as a white solid. IR (KBr) 2954, 1598, 1464, 1385, 1248, 1112, 850, 808 cm$^{-1}$. $^1$H NMR (300 MHz, CDCl$_3$)δ 7.91 (d, J=8.0 Hz, 4H), 7.61 (d, J=7.9 Hz, 4H), 7.45 (½ABq, J=8.3 Hz, 8H), 7.40 (½ ABq, J=8.8 Hz, 8H), 6.98 (s, 4H), 0.20 (s, 36 H). Calc'd for C$_{61}$H$_{64}$S$_4$; 908.4085. Found: 908.4102.

We claim:
1. A compound of the formula

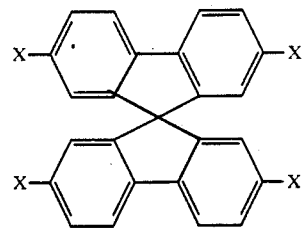

wherein X is a reactive group through which conducting or pro-conducting polymeric subunits can be bonded to the compound selected from the group consisting of bromine, iodine, —O—SO$_2$—CF$_3$, and reactive groups comprising one or more polymer subunits terminally substituted with bromine, iodine or —O—SO$_2$—CF$_3$.

2. A compound according to claim 1, wherein X is bromine.

3. A compound according to claim 1, wherein X is (phenyl)$_n$Br and n is zero or an integer.

4. A method of preparing a compound of the formula

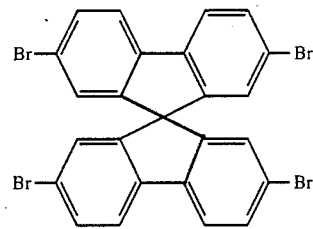

comprising the steps of
(a) reacting a compound of the formula

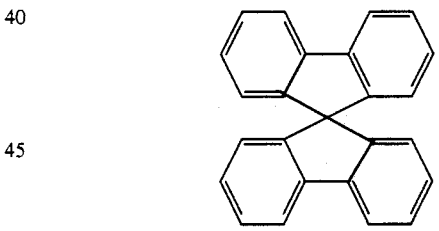

with bromine in the presence of FeCl$_3$ as a catalyst.

* * * * *